US006329426B1

(12) United States Patent
Ueno

(10) Patent No.: US 6,329,426 B1
(45) Date of Patent: Dec. 11, 2001

(54) METHOD FOR TREATING OCULAR HYPERTENSION OF GLAUCOMA

(75) Inventor: Ryuji Ueno, Hyogo (JP)

(73) Assignee: R-Tech Ueno, Ltd., Osaka (JP)

( * ) Notice: Subject to any disclaimer, the term of this patent is extended or adjusted under 35 U.S.C. 154(b) by 0 days.

(21) Appl. No.: 09/220,847

(22) Filed: Dec. 28, 1998

Related U.S. Application Data

(63) Continuation-in-part of application No. PCT/JP98/04399, filed on Sep. 30, 1998.

(30) Foreign Application Priority Data

Oct. 13, 1997 (JP) .................................................. 9-278540

(51) Int. Cl.$^7$ ...................... A61K 31/215; A61K 31/557
(52) U.S. Cl. .......................... 514/530; 514/573; 514/913
(58) Field of Search .................................... 514/530, 573, 514/913

(56) References Cited

U.S. PATENT DOCUMENTS

| 5,001,153 | 3/1991 | Ueno et al. ........................... 514/530 |
| 5,296,524 | 3/1994 | Waters ................................. 523/319 |

FOREIGN PATENT DOCUMENTS

| 0603800AI | 6/1994 | (EP) . |
| 0 603 800A | 5/1994 | (WO) . |
| WO 97 23225 | 7/1997 | (WO) . |
| WO/97/23225 | 7/1997 | (WO) . |

OTHER PUBLICATIONS

G. Resul et al Structure–Activity Relationship of Prostaglandin Cardiovasscular & Renal–Overiew, 781–795, 1993 Current Drugs Ltd.

C. Camras et al "Initial Clinical Studies with Prostaglandins and Their Analogues" Survey of Ophthalmology vol. 41 [Suppl 2]:S61–68, 1997.

J. Stjernschantz et al "Phenyl substituted prostaglanding analogs for glaucoma treatment" Drugs of the Future 17(8): 691–704, 1992.

J. Stjernschantz et al Preclincal Pharmacology of Latanoprost, a Phenyl–Substitued PGF 2 Analogue, Advances in Prostaglanding, Tromboxane, and Leukotrience Research vol. 23: 513–518, 1995.

B. Resul et al "Structure–Activity Relationships and Receptor Profiles of Some Ocular Hypotensive Prostanoids" Survey of Ophthalmology vol. 41 [Suppl 2]: S47–S52, 1997.

M. Hellburg et al "Preclinical Efficacy of AL–6221, a Potent and Selective FP Prostaglanding Agnist" IOVS, Mar. 15, 1998, vol.39, No. 4:1961–8:45.

G. Selen et al "Prostaglanding–Induced Iridial Pigmentation in Primates" Survey of Ophthalmology vol.41 [Suppl 2]:S125–S128, 1997.

P. Wistrand et al "The Incidence and Time–Course of Latanoprost–Induced Iridial Prigmentation as a Fuction of Eye Color" Survey of Ophthalmology vol.41 [Suppl 2]:S129–138, 1997.

J.Rowe et al "Brief Reports:Adverse Side Effects Associated with Lantanoprost" American Journal of ophthalmology vol. 124,No.5:683–685, 1997.

R. Warwar et al "Cystoid Macular Edema and Anterior Uveitis Associated with Lantanoprost Use" Ophthalmology vol. 105,No.2:263–268, 1998.

T. Nakajima et al Abstract of the 6th Meeting of Japanese Glaucoma Society, 136, 1995.

Y. Goh et al "Pharmacological Characterization of Prostaglandin–Related Ocular Hypotensive Agents" Jpn J Ophthalmol vol.38:236–245, 1994.

Toris C. B. et al. "Prostaflandins: A new class of aqueous outflow agents." Ophthalmology Clinics of North America. Sep. 26, 1997; 10/3 (pp. 335–355) Xp000997423.

*Primary Examiner*—Zohreh Fay
(74) *Attorney, Agent, or Firm*—Sughrue, Mion, Zinn, Macpeak & Seas, PLLC

(57) ABSTRACT

By combined administration of a non-FP receptor agonist type prostaglandin compound, for example isopropyl unoprostone, and a FP-receptor type prostaglandin compound, for example Latanoprost, the ocular hypotensive effect of the prostaglandin compounds is enhanced synergistically.

6 Claims, 1 Drawing Sheet

Mean ± S.E.

\* $p<0.05$, \*\* $p<0.01$ : compared with non-treatment [baseline] group (Student' t-test)
\#\# $p<0.01$ : compared with isopropyl unoprostone group in Fig.1 (A) (Student' t-test)
† $p<0.05$, †† $p<0.01$ : compared with latanoprost group in Fig.1 (C) (Student' t-test)

METHOD FOR TREATING OCULAR HYPERTENSION OF GLAUCOMA

RELATED APPLICATIONS

This is a continuation-in-part application of international application PCT/JP98/04399, filed Sep. 30, 1998, which claims priority from Japanese Patent Application No. 278540/1997, filed Oct. 13, 1997.

BACKGROUND OF THE INVENTION

1. Field of the Invention

The Present invention provides a method of treating ocular hypertension or glaucoma. Particularly, the invention provides a method, which can enhance the effect of known compounds synergistically and can reduce the occurrence of unfavorable side effects.

2. Related Art

Among prostaglandin compounds (hereinafter referred as "PG" or "PGs") having 20 carbon atoms in their basic structure and being called "eicosanoids", $PGF_2$ α and $PGF_2$ α a isopropyl ester have been known to have an ocular hypotensive activity (Bahram Resul and Johan Stjernschantz "Structure-Activity Relationships of Prostaglandin Analogues as Ocular Hypotensive Agents" Cardiovascular & Renal-Overview, 781–795 1993, Current Drugs Ltd.; Carl B. Camras et al., *Survey of Ophthalmology* Vol.41 [Suppl 2], S61–S68, 1997, the disclosures of all of these prior arts are herein expressly incorporated by reference). These compounds have been tried in the treatment of glaucoma and ocular hypertension. However, because of their side effects, including a transient increase in intraocular pressure preceding their ocular hypotensive effect, and strong hyperemia of conjunctiva and ocular stimulation, they have not been applied for clinical use so far. Generally, it has been believed that the biological and pharmacological effect of a PG is expressed via a receptor specific to the PGF. $PGF_2$ α and $PGF_2$ α isopropyl ester are known to have high affinity for the FP receptor, i.e. they act as FP receptor agonists (Bahram Resul et al., *Survey of Ophthalmology* Vol.41 [Suppl 2], S47–S52, 1997, the disclosures of this prior art is herein expressly incorporated by reference). In addition, a novel prostaglandin compound which acts as a FP-receptor agonist has also been reported (M. Hellberg et al. *IOVS* vol. 39 No. 4, 1961 Mar. 15, 1998, the disclosure of this prior art is expressly incorporated by reference).

Recently, Latanoprost (general name), a FP-receptor agonist type PG compound which has a high affinity for the FP receptor, has been developed during the study of the ocular hypotensive effect of PGF, a isopropylester. Latanoprost has a basic structure with a different number of carbon atoms from eicosanoids. The structure of Latanoprost is (+)-isopropyl-Z-7-{(1R,2R, 3R, 5S)-3, 5-dihydroxy-2-[(3R)-3-hydroxy-5-phenylpentyl] cyclopentyl}-5-heptenoate. This compound has been reported to have an ocular hypotensive activity (Johan Stjerschantz et al., *Drugs of the Future* vol. 17, No. 8, 691–704, 1992; Johan Stjerschantz et al., *Advances in Prostaglandin, Thromboxane, and Leukotriene Research*, vol. 23 513–518, 1995; EP-A0364417 (corresponds to U.S. Pat. No. 5,296,504 and JP-A-03–501025), the disclosures of all of these prior arts are herein expressly incorporated by reference). However, the desired effect of Latanoprost has not been segregated from hyperemia of conjunctiva, an adverse side effect, and other side effects including iris pigmentation, uveitis and macula edema have also been reported (Goran Selen et al., *Survey of Ophthalmology* vol. 41, [Suppl 2], S125–S128, 1997; Perj Wistrand et al., *Survey of Ophthalmology* vol. 41, [Suppl 2], S129–S138, 1997; Jonathan A. Rowe et al. *American Journal of Ophthalmology* vol. 124, No. 5 683–685, 1997; Ronald E. Warwar et al., *Ophthalmology* vol. 105, No. 2, 263–268, 1998, the disclosures of all of these prior arts are herein expressly incorporated by reference). Further, it was reported recently that the FP receptor may play a significant role in iris pigmentation(Tadashi Nakajima et al., *Abstract of The 6 th Meeting of Japanese Glaucoma Society*, 136, 1995, the disclosure of this prior art is herein expressly incorporated by reference).

On the other hand, there are some non-FP receptor agonist type PG compounds, such as compounds having high affinity for the DP receptor or no substantial affinity for conventional PG receptors, known to have an ocular hypotensive activity (Carl B. Camras et al., Id). Compounds which do not have substantial affinity for conventional PG receptors include isopropyl unoprostone (general name) (Yasumasa Goh et al. *Japanese Journal of Ophthalmology* vol. 38, 236–245, 1994, the disclosure of this prior art is herein expressly incorporated by reference.) The structure of isopropyl unoprostone is (+) isopropyl-Z-7-[(1R,2R,3R,5S)-3, 5-dihydroxy-2(3-oxeodecyl)cyclopentyl] hept-5-enoate and is classified as a docosanoid having 22 carbon atoms in its basic structure. This compound is also known as one of PG metabolites since it has an oxo-group in place of hydroxy group on the carbon atom of position 15 (a so called "15-keto" type) and the carbon atoms of the positions 13 and 14 are linked through a carbon-carbon single bond(a so called "13,14-dihydro" type). The fact that this compound has an ocular hypotensive activity was described in EP-A-0308135 (corresponding to U.S. Pat. No. 5,001,153 and JP-A-02–108, the disclosures of these prior arts are herein expressly incorporated by reference).

The prior art does not describe nor suggest the combination of a FP receptor agonist type PG compound and a non-FP receptor agonist type PG compound, or any synergistic effects between these compounds. There is no teachings that the combination may reduce adverse side effects.

SUMMARY OF THE INVENTION

An object of the present invention is to provide a method of treating ocular hypertension or glaucoma, especially a method which can provide a synergistic effect and reduce adverse side-effects. The present invention also provides a composition for the treatment of ocular hypertension or glaucoma suitable for practicing the present method, and the use of specific compounds for the preparation of said composition.

During an extensive study about possibility of improving the effect by the combination of non-FP receptor agonist type PGs and a variety of compounds, the inventor surprisingly found that the effect can be synergistically enhanced by the combination of a non-EP receptor agonist type PG compound and a FP receptor agonist type PG compound, and that adverse side effects can be reduced.

Thus, the present invention provides a method of treating ocular hypertension or glaucoma comprising a step of administrating to a subject in need of such treatment:

(a) a non-FP receptor agonist type prostaglandin compound, and (b) a FP receptor agonist type prostaglandin compound.

In another aspect, the present invention provides a composition useful for treatment of ocular hypertension or glaucoma comprising (a) a non-FP receptor agonist type prostaglandin compound, and (b) a FP receptor agonist type prostaglandin compound.

In a further aspect, the present invention provides a use of
(a) a non-FP receptor agonist type prostaglandin compound, and
(b) a FP receptor agonist type prostaglandin compound, for preparing a pharmaceutical composition for the treatment of ocular hypertension or glaucoma.

The compound used for component (a) in the present invention may be any non-FP receptor agonist type PG compound insofar as it does not have substantial affinity for the FP receptor and does not act as a FP receptor agonist. It includes, for example, a compound having high affinity for the DP receptor or a compound which does not have substantial affinity for conventional PG receptors, with a compound that does not have substantial affinity for conventional PG receptors being preferable. Examples of the compound having high affinity for the DP receptor are $PGD_2$, BW245C, etc. Examples of the compound that does not have substantial affinity for conventional PG receptors include 15-keto-PG compounds, which is so-called metabolic type PG-compounds, preferably, 13,14-dihydro-15-keto-PGs, for example, isopropyl unoprostone.

The compound used for component(b) in the present invention may be any FP receptor agonist type PG compound insofar as it has high affinity for the FP receptor and acts as a FP receptor agonist, preferably the PG compounds which can have affinity for the FP receptor as described in the above cited prior arts, especially $PGF_2$ α, $PGF_2$ αisopropyl ester, Latanoprost, AL6221, AL5848, AGN-191129 and AGN-191910 may be preferably used as component(b).

The present invention may be applied to the treatment of various diseases and conditions in which reduction of intraocular pressure is desired, for example, glaucoma, ocular hypertension and the other diseases accompanied by increased intraocular pressure. The term "treatment or treating" in this specification and claims refers to any means of control, including preventing or curing the disease, relieving or alleviating the condition, and arresting the development of the condition.

In the present invention, the term "a subject in need of such treatment" means a subject who is suffering from a disease in which a reduction in his/her intraocular pressure is desirable, for example, glaucoma and ocular hypertension, or a subject who is susceptible to suffering from such disease as discussed above.

According to the present invention, the combination of the components (a) and (b) provides a synergistic effect. That is, since the combination enhances the desired effects of the components (a) and (b) synergistically, the dose of the each component can be reduced and, therefore, adverse side effects can be effectively reduced.

According to the present invention, the method of the administration can be in the form of an ophthalmic composition comprising the components (a) and (b).

In the present composition, the ratio of (a):(b) is not limited but in general about 1:0.005–1:2, preferably, about 1:0.01–1.

The dose of each component in the present invention should be determined by a doctor according to, such as, the state and severity of the condition to be treated, the object of treatment and total amount of the administration. Typically, the amount of the component (a) in the composition used for topical administration is about 0.005–2 wt %, preferably, 0.01–1 wt %. The amount of the component (b) in the composition used for topical administration is about 0.0001–2 wt %, preferably, 0.0005–1 wt %. The components (a) and (b) may be administered either simultaneously or individually.

The composition of the present invention may be formulated to contain both of the components (a) and (b) in a single dosage unit, or may be a package consisting of separate dosage units containing each component respectively. The composition of the present invention may further contain any conventional compound used in ophthalmologic field such as carrier and adjuvant.

The composition of the present invention may be formulated as liquids such as solution, emulsion, and suspension, or as semisolids such as gel or ophthalmic ointment.

Examples of diluents for an aqueous solution or suspension include distilled water and physiological saline. Examples of diluents for a non-aqueous solution or suspension include vegetable oil, liquid paraffin, mineral oil, propylene glycol and p-octyldodecanol and the like. In addition, isotonic agents, such as sodium chloride, boric acid and sodium citrate to make isotonic with the lacrimal fluid, and buffering agents, such as borate buffer and phosphate buffer to maintain pH about 5.0 to 8.0 may be contained in the present composition. Further, stabilizing agents such as sodium sulfite and propylene glycol, cheating agents such as sodium edetate, thickening agents such as glycerin, carboxymethyl cellulose and carboxyvinyl polymer, and preservatives such as methyl paraben, propyl paraben may be contained in the composition. The ingredients are sterilized by means of, for example, passing through a bacterial filter or heating.

The ophthalmic ointment may contain, such as, vaseline, Zelen 50, Plastibase and Macrogol as base components and a surfactant for increasing hydrophilicity. It may also contain gelling agents such as carboxymethylcellulose, methylcellulose, carboxyvinyl polymer, as well.

In addition, the composition may contain antibiotics such as chloramphenicol and penicillin.

BRIEF DESCRIPTION OF THE DRAWINGS

FIG. 1 (B) shows a time course of intraocular pressure followed by a single instillation of 0.003% Latanoprost at 10 o'clock.

FIG. 1 (C) shows a time course of intraocular pressure followed by a single instillation of 0.003% Latanoprost at 22 o'clock.

FIG. 1 (D) shows a time course of intraocular pressure followed by the combined instillation of 0.003% Latanoprost at 22 o'clock and 0.06% isopropyl unoprostone at a time 12 hours after that.

Figure 1:
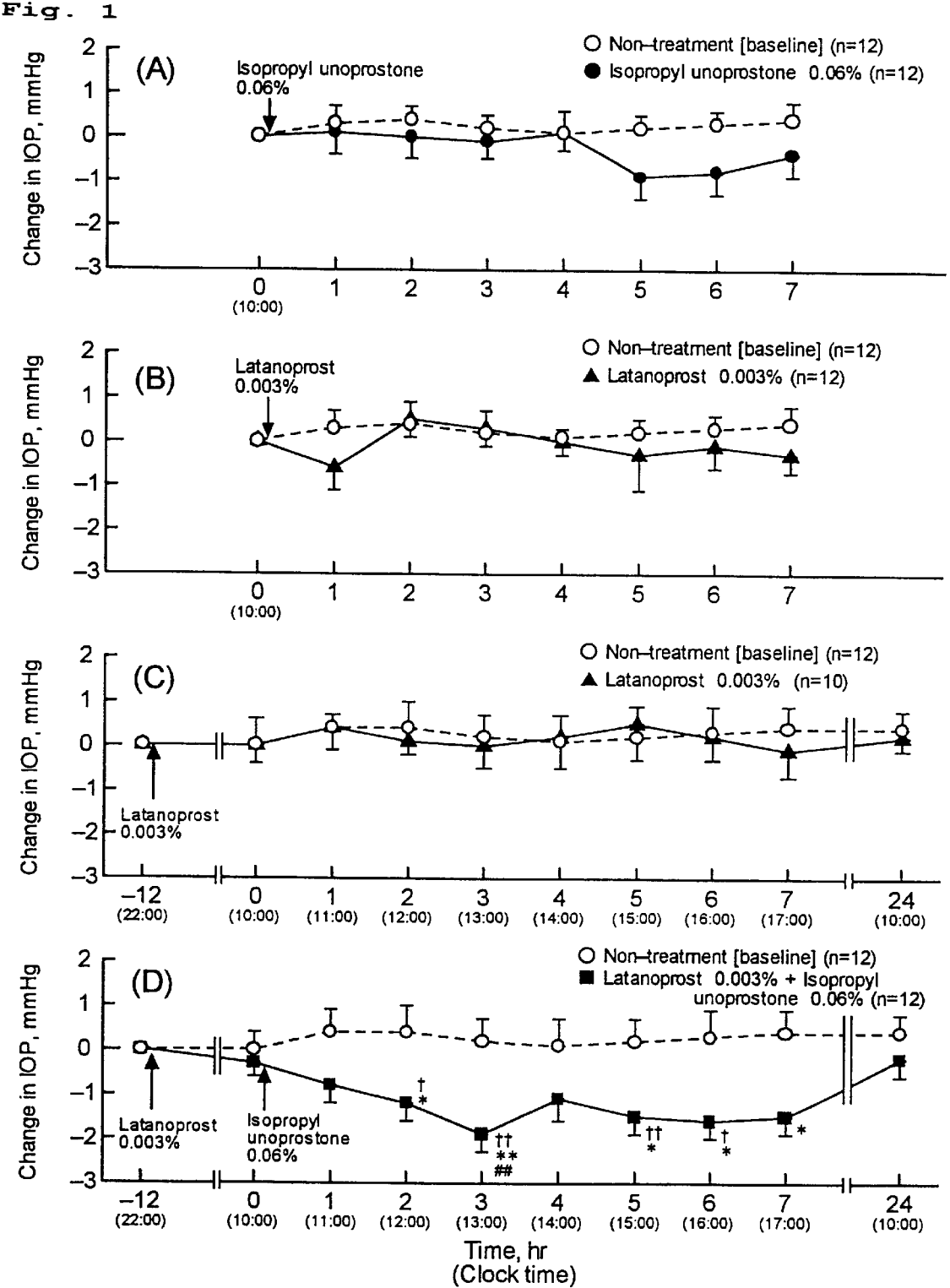
FIG. 1 (A) shows a time course of intraocular pressure followed by a single instillation of 0.06% isopropyl unoprostone.

The best mode of performing the present invention.

The present invention will be illustrated in more detail by the following examples.

TEST EXAMPLE

1. Test Substance

In order to study the ocular hypotensive effect of the combined administration of isopropyl unoprostone and Latanoprost, 0.06% isopropyl unoprostone eye drops and 0.003 % Latanoprost eye drops were prepared separately. Each concentration of the active ingredients is about a half of conventional clinical composition.

2. Animal

Male normal cynomolgus monkeys (body weight of 4.5–6.5 kg) having good health and fore eye condition were used.

3. Administration schedule

Each of isopropyl unoprostone and Latanoprost eye drops was administrated topically to the respective monkeys by means of micro pipette (Gilson, U.S.A) in an amount of 30 $\mu$1 per eye at 10 o'clock. For clinical use, Latanoprost was directed to administrate once a day at night, and it was reported from an examination with normal volunteers that the maximum decrease of intraocular pressure occurred about 12 hours after the administration. Therefore, in this example, the effect of Latanoprost eye drops on intra ocular pressure when administrated at 22 o'clock were also determined. For the combination eye drop of isopropyl unoprostone and Latanoprost, Latanoprost eye drops were administrated at 22 o'clock and then isopropyl unoprostone were administrated at 10 o'clock in the next morning, that is 12 hours after latanoprost administration.

4. Measurement of Intraocular Pressure

The monkeys were anesthetized intramuscularly with 5.0–7.5 mg/kg of Ketamin (Sankyo Pharmaceuticals Co. Ltd.). A time course of the intraocular pressure was determined under topical anesthetization by dropping 0.4% oxybuprocaine hydrochloride to eyes (Santen Seiyaku), by means of applanation pneumatonograph (Nippon Alcon).

5. Results

Changes in intraocular pressures ($\Delta$ TOP) of each administration group compared with the pressure determined before the administration and are shown in FIG. 1 (A)).

Single ocular administration of 0.06% isopropyl unoprostone did not show any significant change in IOP when compared with a control (non-treatment) group (FIG .1 (A)).

Single ocular administration of 0.003% Latanoprost at 10 o'clock (FIG. 1 (B)) nor at 22 o'clock (FIG. 1(C)) did not show any significant change in IOP when compared with the control(non-treatment) group.

On the contrary, when 0.003% Latanoprost was administrated at 22 o'clock and 0.06% isopropyl unoprostone was administrated at 10 o'clock the next morning, that is 12 hours after Latanoprost administration (combined administration), the combination showed a significant decrease of IOP compared with any one of the groups of control(non-treatment), single administration of isopropyl unoprostone, and single administration of Latanoprost (FIG. 1 (D)).

From the above results, it is demonstrated that the combined administration of isopropyl unoprostone and Latanoprost decreases intraocular pressure synergistically.

From the above results, it can be said that a synergistic ocular hypotensive effect will be obtained from the combination of the components (a) and (b).

Industrial Applicability

The present invention is useful for treatment of ocular hypertension and glaucoma.

What is claimed is:

1. A method of treating ocular hypertension or glaucoma, which comprises the step of administering, to a subject in need of such treatment, (a) a non-FP receptor agonist type Prostaglandin compound, and (b) a FP receptor agonist type prostaglandin compound.

2. The method of claim 1, wherein said (a) non-FP receptor agonist type prostaglandin compound and said (b) FP agonist type prostaglandin compound are administered simultaneously in a single dosage unit.

3. The method of claim 1, wherein said (a) non-FP receptor agonist type prostaglandin compound and said (b) FP receptor agonist type prostaglandin compound are administrated individually in separate dosage units.

4. The method of claim 1, wherein said non-FP receptor agonist type prostaglandin compound is a 13,14 dihydro-15-keto-prostaglandin compound.

5. The method of claim 1, wherein said non-FP receptor agonist type prostaglandin compound is isopropyl unoprostone.

6. The method of claim 1, wherein said FP receptor agonist type prostaglandin compound is Latanoprost.

* * * * *

UNITED STATES PATENT AND TRADEMARK OFFICE
CERTIFICATE OF CORRECTION

PATENT NO. : 6,329,426 B1
DATED : December 11, 2001
INVENTOR(S) : Ryuji Ueno

It is certified that error appears in the above-identified patent and that said Letters Patent is hereby corrected as shown below:

Column 6,
Lines 16 - 20, delete Claim 1 and insert the following:
 A method of treating ocular hypertension or glaucoma, which comprises the step of administering, to a subject in need of such treatment, (a) a non-FP receptor agonist type Prostaglandin compound which is a 15-keto-prostaglandin, and (b) a FP receptor agonist type prostaglandin compound.

Signed and Sealed this

Twentieth Day of May, 2003

JAMES E. ROGAN
*Director of the United States Patent and Trademark Office*